United States Patent [19]

Klein

[11] Patent Number: 4,568,637
[45] Date of Patent: Feb. 4, 1986

[54] METHOD OF DETERMINING ANTIBIOTICS IN BIOLOGICAL LIQUIDS

[75] Inventor: Hilton J. Klein, Thurmont, Md.

[73] Assignee: Whittaker M.A. Bioproducts, Inc., Walkersville, Md.

[21] Appl. No.: 521,857

[22] Filed: Aug. 10, 1983

[51] Int. Cl.⁴ ............................................. C12Q 1/34
[52] U.S. Cl. ...................................... 435/18; 435/32; 435/231
[58] Field of Search ............................. 435/18, 231, 32

[56] References Cited

U.S. PATENT DOCUMENTS

| | | | |
|---|---|---|---|
| 3,063,916 | 11/1962 | Kosikowski | 435/32 |
| 3,126,325 | 3/1964 | Poole | 435/32 |
| 3,644,177 | 2/1972 | Zyk | 435/18 |
| 3,830,700 | 8/1974 | O'Callaghan et al. | 435/18 |
| 4,239,745 | 12/1980 | Charm | 436/501 |
| 4,448,880 | 5/1984 | Schindler et al. | 435/18 |

FOREIGN PATENT DOCUMENTS

| | | | |
|---|---|---|---|
| 0489866 | 1/1951 | Canada | 435/231 |
| 0034759 | 9/1981 | European Pat. Off. | 435/18 |
| 0037932 | 10/1981 | European Pat. Off. | 435/18 |
| 2049681 | 12/1980 | United Kingdom | 435/18 |

OTHER PUBLICATIONS

Voller et al., Journal of Clinical Pathology 1978, vol. 31, pp. 507-520.
Thornsberry et al., Antimicrobial Agents and Chemotherapy, Nov. 1974, vol. 6, No. 5, pp. 653-654.
O'Callaghan et al., Antimicrobial Agents and Chemotherapy 1972, vol. 1, No. 4, pp. 283-288.
Rosenblatt et al., American Journal of Clinical Pathology, 1978, pp. 351-354.

*Primary Examiner*—Sam Rosen
*Assistant Examiner*—William J. Herald
*Attorney, Agent, or Firm*—Donald E. Nist

[57] ABSTRACT

The presence of beta lactam ring-containing cephalosporins and penicillin is determined in biological liquids such as milk by contacting the test liquid with a beta lactam ring-containing chromogenic compound (such as nitrocefin) and penicillinase and measuring the color developed in the test liquid in comparison with a color standard.

7 Claims, 1 Drawing Figure

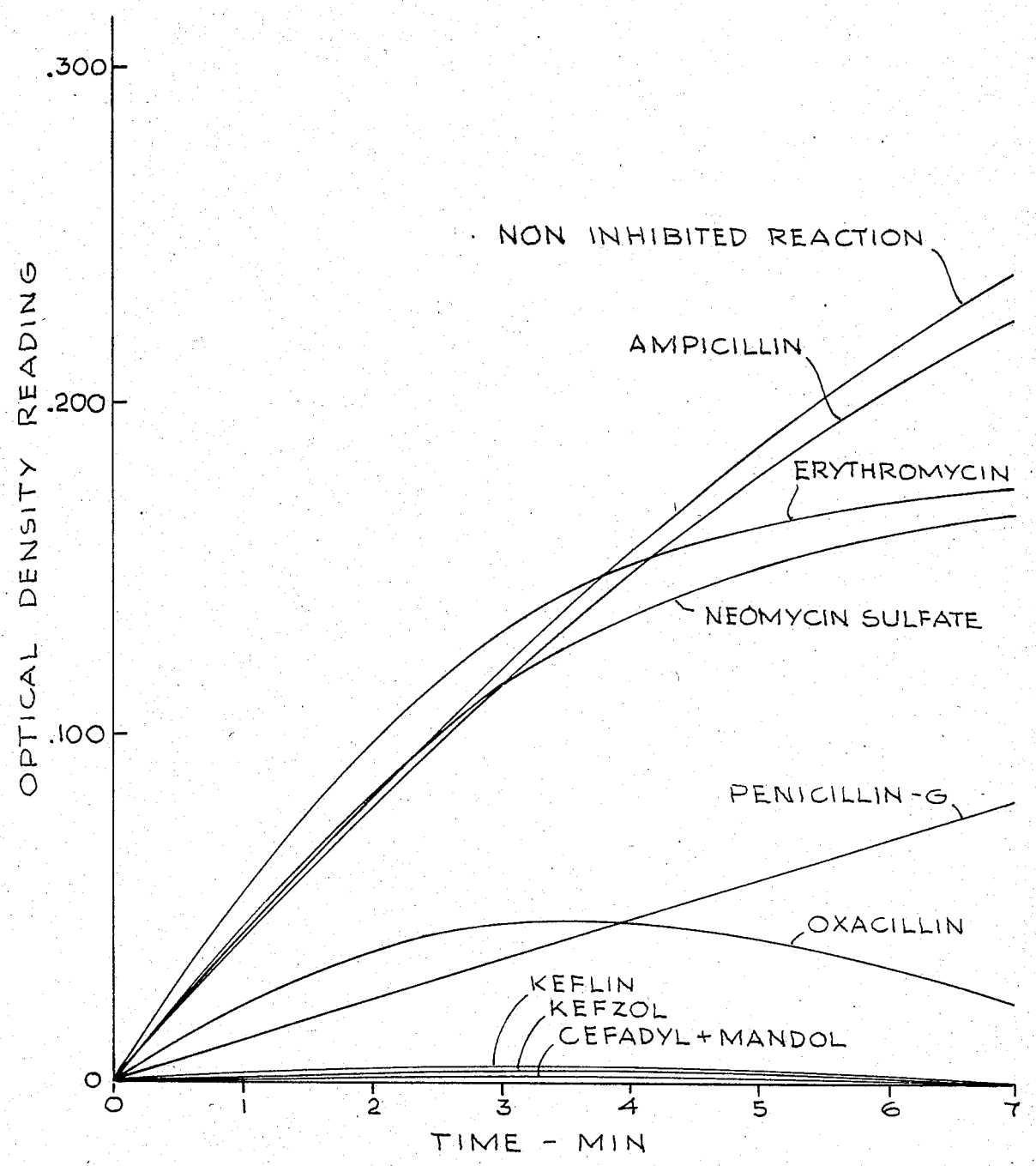

METHOD OF DETERMINING ANTIBIOTICS IN BIOLOGICAL LIQUIDS

BACKGROUND OF THE INVENTION

1. Field of the Invention

The present invention generally relates to antibiotics and more particularly to an improved method of determining the presence of beta lactam ring-containing cephalosporins and penicillin in biological liquids and the like.

2. Prior Art

Various serologic and microbiological assays have been employed for detecting penicillin and cephalosporins in such biological liquids as milk and urine. Serologic procedures include radioimmunoassays and enzyme immunoassays, while microbiological assays employ conventional culture and sensitivity methodology.

Radioimmunoassays and enzyme immunoassays are relatively expensive and time consuming. Each method requires specialized and expensive equipment not commonly found in a dairy processing or microbiology laboratory. Standard microbiological procedures are also relatively expensive and time consuming to perform. All such methods require highly trained, competent technicians to perform the assays and interpret the results. Moreover, the time required to perform such assays varies from several hours for enzyme immunoassay procedures to up to two days for microbiological procedures. Serologic procedures have the additional disadvantage in that they do not discriminate between biological active molecules and biologically inactive residues of the molecules being tested for, that is pencillin and cephalosporins.

In view of the large number of assays currently being required on milk and urine and other biological liquids to determine the presence of penicillin and cephalosporins therein, it would be highly beneficial to be able to provide a more rapid, effective and efficient procedure for making such determinations. Preferably such improved method should be capable of being run accurately on readily available, relatively inexpensive equipment by relatively unskilled personnel.

SUMMARY OF THE INVENTION

The improved method of the present invention satisfies all the foregoing needs. It is an extremely rapid procedure which requires only about fifteen minutes to perform. No specialized equipment beyond that found in most laboratories is needed to perform an assay using the present method. No spectrophotometric reader, or radioactive particle counting equipment or live bacterial cultures are required. Highly skilled technical expertise is also not required either to perform the test or to interpret the results. The test is far less expensive to perform than conventional tests, considering the equipment, technical expertise and reagents needed for the test. The test detects biologically active penicillins and beta lactam ring-containing cephalosporins with a degree of sensitivity which is required for testing milk samples in the dairy industry.

The method involves contacting the test liquid with a beta lactam ring-containing chromogenic compound and penicillinase. The penicillinase breaks any beta lactam rings present to cause the chromogenic compound to exhibit color. Any penicillin and any beta lactam ring-containing cephalosporin present also have their beta lactam rings attacked by the penillinase so that as the concentration of such antibiotics in the test liquid increases, the rate and extent of color development in the chromogenic compound decreases, serving as an accurate measure of the presence of such antibiotics in the test liquid and their concentration.

In carrying out the test the color development in the test liquid is compared against a color standard. Preferably, the color standard comprises a control which contains all the components used in the test and in their same relative proportions except that the control liquid, although of the same type as the test liquid, is devoid of such antibiotics. The control is permitted to develop color over the same time period as the test liquid, so that a direct color comparison between the color developed in the test liquid and that of the control can be made on a colorimeter.

The chromogenic compound preferably is nitrocefin and is preferably present on a solid phase substrate such as an absorbent pad or disc or the like. The test procedure usually is carried out at about room temperature and over a period of about 3 to 7 minutes.

Further features of the present invention are set forth in the following detailed description and the accompanying drawings.

DRAWINGS

The single FIGURE of the drawings is a graph plotting optical density readings on a colorimeter against time for a plurality of antibiotics tested in accordance with the present method.

DETAILED DESCRIPTION

The improved method of the present invention comprises contacting a biological liquid to be tested with a beta lactam ring-containing chromogenic compound and penicillinase for a predetermined period of time, and then measuring the amount of color developed in the test liquid at the end of the time period in comparison with a color standard, thereby determining the presence or absence of beta lactam ring-containing cephalosporins, penicillin and mixtures thereof.

The liquid to be tested can be any liquid but usually is a biological liquid such as milk, urine or the like. The beta lactam ring-containing chromogenic compound is one in which, when the beta lactam ring is broken, the compound exhibits a color which can be read easily, as in a colorimeter or the like. It has been found that the chromogenic compound which is known as nitrocefin and which has the following chemical formula is preferred for this purpose: 3-(2,4-dinitrostyryl)-(6R,7R)-7-(2-thienylacetoamido)-ceph-3-em-4-carboxylic acid. Other beta lactam ring-containing chromogenic indicators which function in a similar manner could be substituted for the nitrocefin in the present method.

Penicillins such as penicillin G chloroprocaine, penicillin O, phenoxymethylpenicillin, potassium, alpha-phenoxyethylpenicillin, sodium methicillin and other penicillins can be tested for. Beta lactam ring-containing cephalosoporins, such as ampicillin, oxacillin, Keflin, Kefzol, Cefadyl and Mandol, can be tested for as well as the penicillin by the present method. Other beta lactam ring-containing cephalosporins can also be tested for by the present method. Keflin is the U.S. registered trademark of Eli Lilly and Company for the antibiotic cephalothin (sodium salt thereof). Kefzol is the U.S. registered trademark of Eli Lilly and is sodium cefazolin. Cefadyl is the registered U.S. trademark of Bristol Laboratories and is sodium cepharirim. Mandol is the U.S. registered trademark of Eli Lilly and is the defamandole nafate.

Penicillinase is a term applied to enzymes which antagonize the antibacterial action of penicillin. Such enzymes are found in many bacteria and have the effect of attacking the beta lactam ring of the penicillin and also the same ring of cephalosporins. Penicillinase also attacks the beta lactam ring of the chromogenic compound used in the present test method.

In carrying out the present method, the test liquid, such as milk, is added to a suitable reaction vessel, such as a cuvette or microtiter plate well. Penicillinase in a concentration such as 100 units per milliliter in phosphate buffered saline (PBS) having a pH of 7.4 and 0.01 M is added ot the test liquid in the reaction vessel, after which the chromogenic indicator, nitrocefin, is added to the reaction vessel and the contents are thoroughly mixed for one minute.

A control may also be disposed in another well of the reaction vessel. The control contains the same concentration of a liquid which is the same type as the test liquid, as for example, milk, but is known to have no antibiotic present. The control is provided with the same concentration of penicillinase and chromogenic indicator as the test well and mixed for the same period of time so that any color reactions occurring in the test well can be read against the color reactions in the control well. It is not necessary to know the concentration of the color indicator or penicillinase so long as the same amount is used in the test sample and the control.

When the test well contains a test liquid which has either penicillin or beta lactam ring-containing cephalosporin present, the color development in that well will be either reduced or totally suppressed in comparison with a color development in the control well. The reason for this is that penicillin and beta lactam ring-containing cephalosporins will correspondingly compete with the color indicator regarding enzymatic breakdown of the beta lactam rings thereof by the penicillinase. The nitrocefin exhibits a red color when its beta lactam ring is borken and this color develops after an appropriate incubation period of about 3–15 minutes at about room temperature, for example, about 70°–80° F.

The color in test well and the color in the control well are read by a colorimeter, spectrophotometer or the like, or can be evaluated visually after the incubation period. Sensitivity of the reaction can be adjusted by altering the concentrations of the ingredients and adjusting the incubation times and temperatures. It has been found that the test can be conveniently carried out by reading the color reaction at the end of three minutes and seven minutes after contacting of the ingredients is initiated and the reaction begins. When a spectrophotometer is used, the test and control solutions can be measured at a wave length of 482 nm. One can also measure the decrease in the amount of absorption of the sample using a spectrophotometer set to read at a wave length of 408 nm. It is also possible to quantitatively determine the relative concentration of penicillin and beta lactam ring-containing cephalosporins, at least to some extent, using the present method by determining the degree of suppression of color development as compared with the control sample. It is further possible to provide color standards which are made up synthetically rather than running a control parallel to the test. The chromogenic cephalosporin used after The chromogenic color indicator used in the present method can contact the reagent mixture while the indicator is in solution or disposed on a solid phase such as on an absorbent disc or particulate surface of the like, that is bout to, coated on, or impregnated in such solid substrate. Sticks, psears, discs, etc., can be made up bearing a uniform and either known or unknown concentration of chromogenic cephalosporin and can be dipped into the mixture of the penicillinase and test liquid to initiate the test reaction.

It will be understood that the present method can be automated so that a large number of raw milk samples, urine samples and the like can be rapidly screened for the presence of the described antibiotics so that economic losses can be minimized. For example, when cattle are treated for various diseases with antibiotics, their milk must be screened to assure that the antibiotics do not appear therein and to assure that any antibiotic-contaminated milk is not added to non-contaminated milk.

The present method can be carried out very rapidly with a high degree of reliability on readily available, relatively inexpensive equipment utilizing a minimum of reagents and requiring a minimum of expertise in order to accurately reproduce reliable results. The following examples further illustrate further features of the present invention.

EXAMPLE I

Penicillin G (1585 U/mg) was made up as an aqueous solution in sterile deionized water at 100 U/ml. Type I Penicillinase solution was made in PBS at concentrations of 100 U, 10 U, and 1 U per ml. Discs uniformly impregnated with a given concentration of the substrate, nitrocefin, were cut into sixths for use in the following testing.

200 ul of each concentration of penicillinase type I were added to each of two wells of a cuvette. This was repeated in triplicate cuvette strips. To two cuvette strips 200 ul of penicillin G (100 U/ml) was added to the wells. Then nitrocefin substrate disc segments were added in a uniform amount to each cuvette well. Timing was initiated with the addition of the first disc segment.

Control wells consisted of:
PBS +nitrocefin disc
PBS+Penicillinase
Penicillin+Penicillinase The blank used for the spectrophotometer contained the nitocefin disc +PBS. The wavelength used as 480 nm. All reactions were carried out at room temperature (19° C.).

Results could be evaluated visually and inhibition of the penicillinasenitrocefin reaction by penicillin G was evident after 3 minutes in the 100 U penicillinase concentration wells. No inhibition could be seen at 8 minutes or later. Color changes and inhibition were evident in the 10 U penicillinase wells (inhibition) but not in the 1 U penicillinase wells at 8 minutes.

By 15 minutes after initiation of incubation, no difference was observed in the 100 U and only a slight difference was observed in the 10 U penicillinase wells, but a change was easily evident in the 1 U wells visually. Optical Density values are listed below in Table I to correspond with these evaluations.

TABLE I

| TIME 8 MINUTES - Optical Density Values (at 480 nm): | | | |
|---|---|---|---|
| | Penicillinase Concentration | | |
| | 100 Units/ml | 10 Units/ml | 1 Unit/ml |
| penicillinase + nitrocefin | 0.603 | 0.543 | 0.397 |
| penicillinase + nitrocefin + Penicillin G | 0.703 | 0.288 | 0.225 |
| TIME - 15 MINUTES: | | | |
| penicillinase + nitrocefin | 2.586 | 3.197 | 2.659 |
| penicillinase + substrate + Penicillin G | 0.833 | 0.598 | 0.596 |

EXAMPLE II

Various antibiotics used for intravenous injection in the treatment of bovine mastitis were tested by the present method. All antibiotics were initially supplied as dry powder and then rehydrated with sterile deionized water prior to use. 300 ul of each antibiotic solution was used in the experiment. All antibiotics were used at a final concentration of 100 ug/ml diluted in PBS. The antibiotics tested were as follows.

| Trade Name: | Generic Name: |
|---|---|
| Keflin | Cephalothin sodium |
| Kefzol | Cefazolin sodium |
| Cephadyl | Cepharirin sodium |
| Mandol | Defamandole nafate |
| Mycifradin | Neomycin sulfate |
| Polycillin-N | Ampicillin sodium |
| Bactocill | Oxacillin sodium |
| Erythrocin | Erythromycin lactobionate |
| | Penicillin-G |

Nitrocefin was used as the chromogenic cephalosporin substrate. Discs uniformly impregnated with preselected concentration of nitrocefin were cut into sixths using scissors and forceps. Each disc Type II penicillinase was used at a concentration of 10 Units/ml diluted in PBS. 300 ul of penicillinase was added to each well as needed.

In each instance the antibiotic solution to be tested was added to a cuvette well, whereupon the penicillinase and the nitrocefin were added to the same well. The contents in the well were then stirred for one minute and the well held at a temperature of about 70° F. Uptical density readings were taken over a period of 7 minutes after the contacting was initiated. The results of those optical density readings are set forth in FIG. 1 of the accompanying drawings and also in summary form in Table II below.

TABLE II

Visual Evaluation of the Inhibition of Various Antibiotics on the Nicrocefin/Penicillinase Reaction

| Sample | Red Color (0–4) |
|---|---|
| Keflin | 0 |
| Kefzol | 0 |
| Cefadyl | 0 |
| Mandol | 0 |
| Mycifradin (Neomycin sulfate) | 4 |
| Polycillin-N (Ampicillin sodium) | 3 |
| Bactocill (Oxacillin sodium) | 1 |
| Erythrocin (Erythromycin lactobionate) | 4 |
| Penicillin-G | 2 |
| CONTROLS: | |
| Disk + PBS only | 0 |
| Disk + Enzyme only | 4 |

0 = complete inhibition
4 = no inhibition

It will be noted that no reaction occurred where the chromogenic-bearing disc was present only in the carrier solution as a control. A totally uninhibited maximum reaction occurred when the penicillinase was present only with the chromogenic indicator, also as a control. The beta lactam ring-containing cephalosporins, Keflin, Kefzol, Cephadyl and Mandol all totally inhibited the red color in the test solution. Oxacillin almost completely inhibited the red color while penicillin G substantially inhibited the red color. Ampicillin showed a relatively weak inhibition. Although ampicillin is a beta lactam ring-containing compound, its structure apparently prevents full competitive attack of its beta lactam ring by penicillinase.

The antibiotics erythromycin and neomycin are not beta lactam ring-containing cephalosporins. When the test results were read at the end of three minutes, the erythromycin showed no color inhibition while neomycin showed only a very small color inhibition which apparently was due to the particular nature of its structure. Erythromycin produced a milded color inhibition over a 7 minute test period, which inhibition again was due apparently to the particular chemical structure involved. Accordingly, such a test is read at the end of three minutes, it is substantially completely accurate relative to the presence of penicillin and beta lactam ring-containing cephalosporins. Over a longer test period it may also detect the presence of certain other antibiotics, none of which are desirable to be present in consummable biological liquid such as milk. Therefore, there is an advantage in reading the test results at the end of 7 minutes so that a wider spectrum of antibiotics can be detected in the test sample.

It will be understood from a review of FIG. 1 and the foregoing examples that the present method provides a simple, rapid and effective way of determining the presence of antibiotics in biological liquids and other liquids for that matter, particularly antibiotics having beta lactam rings present. The method can be carried out in a variety of modes by relatively unskilled personnel making visual determinations by the unaided eye or with a colorimeter or spectrophotometer. The determinations are accurate, rapid, inexpensive and easily automated for maximum efficiency. Various other advantages are set forth in the foregoing.

Various modifications, changes, alterations and additions can be made in the present method, its steps and their parameters. All such modifications, changes, alterations and additions as are within the scope of the appended claims form part of the present application.

What is claimed is:

1. An improved method of determining the presence of antibiotic selected from the group consisting of beta lactam ring-containing cephalosporins, penicillin and mixtures thereof in liquids, said method comprising:

a. contacting a liquid to be tested to determine the presence therein of antibiotic selected from the group consisting of beta lactam ring-containing cephalosporins, penicillin and mixtures thereof, with a known sufficient concentration of each of a beta lactam ring-containing chromogenic compound comprising nitrocefin and penicillinase for a time sufficient to develop color in said test liquid when said antibiotic is present therein; and, b. measuring the amount of color developed in said test liquid at the end of said time period in comparison with a color standard, thereby determining the presence or absence of said antibiotic in said test liquid.

2. The improved method of claim 1 wherein said standard is developed by contacting the same concentration of said penicillinase and said chromogenic compound and the same type and concentration of liquid as said test liquid but known to be free of said antibiotic over the same time period.

3. The improved method of claim 1 wherein the relative concentration of antibiotic in said test liquid is determined colorimetrically by reference to said standard.

4. The improved method of claim 1 wherein said liquid comprises a biological liquid.

5. The improved method of claim 4 wherein said liquid comprises milk.

6. The improved method of claim 1 wherein said chromogenic compound is contacted with said test liquid while said chromogenic compound is disposed on a solid phase substrate.

7. The improved method of claim 1 wherein said contacting is carried out at about ambient temperature and said color measuring is carried out at about 3 and 7 minutes after initiating said contacting.

* * * * *